United States Patent [19]

Klimisch et al.

[11] Patent Number: 5,189,067

[45] Date of Patent: Feb. 23, 1993

[54] SKIN TREATMENT WITH SILICONATES

[75] Inventors: Helen M. Klimisch; Thomas H. Lane, both of Midland, Mich.

[73] Assignee: Dow Corning Corporation, Midland, Mich.

[21] Appl. No.: 683,899

[22] Filed: Apr. 11, 1991

[51] Int. Cl.$^5$ .................. A61K 47/00; A61K 31/695
[52] U.S. Cl. ................................. 514/772; 514/784; 514/785; 514/788; 514/847; 514/63
[58] Field of Search ............... 514/847, 772, 784, 785, 514/788, 63

[56] References Cited

U.S. PATENT DOCUMENTS

| | | | |
|---|---|---|---|
| 3,198,820 | 3/1965 | Pines | 260/448.2 |
| 3,816,184 | 6/1974 | Redmore | 148/6.15 |
| 4,235,638 | 11/1980 | Beck | 106/287.12 |
| 4,335,104 | 6/1982 | Van Cleave | 424/59 |
| 4,344,860 | 8/1982 | Plueddemann | 252/389 |
| 4,352,742 | 10/1982 | Davis | 252/75 |
| 4,354,002 | 10/1982 | Davis | 524/588 |
| 4,362,644 | 12/1982 | Davis | 252/389 |
| 4,370,255 | 1/1983 | Plueddemann | 252/389 |
| 4,534,880 | 8/1985 | Kosal | 252/174.13 |
| 4,562,278 | 12/1985 | Hill | 556/418 |
| 5,087,443 | 2/1992 | Chizat et al. | 424/47 |

FOREIGN PATENT DOCUMENTS 87360 10/1988 Luxembourg .

*Primary Examiner*—Frederick E. Waddell
*Assistant Examiner*—M. Moezie
*Attorney, Agent, or Firm*—Jim L. DeCesare

[57] ABSTRACT

A method of treating human skin to enhance the ability of skin in the absorption and retention of moisture in order to retard skin moisture loss. There is applied to skin an organosilicon compound exhibiting humectant-like characteristics which is an anionic siliconate. An alternate method treats human skin to reduce the trans-epidermal water loss of skin in order to increase moisturization and to enhance skin softness. There is applied to skin an occlusive film forming organisilicon compound which is also a siliconate.

10 Claims, No Drawings

SKIN TREATMENT WITH SILICONATES

BACKGROUND OF THE INVENTION

This invention relates to the treatment of human skin with certain organosilicon compounds which are siliconates.

Mineral oil is a highly refined, colorless, tasteless, and odorless liquid mixture of hydrocarbons obtained from petroleum that has been used medicinally as an internal lubricant and in the manufacture of various salves and ointments. It is also known as medicinal oil, white mineral oil, heavy mineral oil, light mineral oil, liquid paraffin and paraffin oil. Mineral oil has long been the emollient of choice in creams and lotions. It is second only to water as a moisturizer ingredient. While mineral oil has been found to be an effective and economical emollient for skin care applications and provides softening, smoothing and a protective action on skin, it nevertheless suffers from the disadvantage that it is easily removed from the skin by washing the skin with soap. Thus the effectiveness and long term benefits of mineral oil enumerated above are of a limited duration. The water content of the outer layers of the stratum corneum of the human skin is a controlling factor in the appearance of dry skin symptoms. When the stratum corneum contains an adequate amount of water within the range of ten to twenty percent the skin remains flexible. However, when the water content falls below ten percent the stratum corneum often becomes brittle and rough and can exhibit scaling and cracking. The stratum corneum receives its water from the deep layers of the epidermis by diffusion or when it is brought into direct contact with water. The diffusion process is controlled by the water content of the skin as was well as the concentration gradient. In a very dry environment, the water loss from the external skin layers can be significant and often exceeds the rate of replacement by diffusion. An occlusive barrier of petrolatum placed onto the surface of the skin acts to retard the water loss to the environment and allows the skin surface to rehydrate by the diffusion process. Due to the effectiveness, low cost, and safety of petroleum derivatives, it serves as a useful occlusive moisturizer and contributes to dry skin prevention by protection and moisture retention, as well as dry skin repair by emolliency, lubricity and moisture restoration. However in accordance with the present invention, it has been discovered that certain organosilicon compounds provide skin care formulations that a consumer can perceive as being beneficial and more aesthetically pleasing.

SUMMARY OF THE INVENTION

This invention relates to a method of treating human skin to enhance the ability of skin in the absorption and retention of moisture in order to retard skin moisture loss. In accordance with the invention there is applied to skin an organosilicon compound exhibiting humectant-like characteristics. The organosilicon compound is an anionic siliconate.

The invention is also directed to a method of treating human skin to reduce the transepidermal water loss of skin in order to enhance moisturization and skin softness. In this embodiment of the invention there is applied to skin an occlusive film forming organosilicon compound. The organosilicon compound again is an anionic siliconate.

These and other features, objects and advantages of the herein described present invention will become more apparent from a consideration of the following detailed description thereof.

DETAILED DESCRIPTION OF THE INVENTION

It has been discovered that human skin can be treated to enhance the ability of skin in the absorption and retention of moisture in order to retard skin moisture loss by applying to skin an organosilicon compound exhibiting humectant-like characteristics.

It has also been discovered that human skin can be treated to reduce the transepidermal water loss of skin in order to enhance skin softness by applying to skin an occlusive film forming organosilicon compound.

In this embodiment, the occlusive film forming organosilicon compound can be applied to the skin as a formulated product, from a solution, or without a solvent as "neat". The average reduction in the rate of transepidermal water loss has been found to be significant.

Anionic siliconates are well known materials and are described in U.S. Pat. Nos. 3,198,820, 3,816,184, 4,235,638, 4,344,860, 4,352,742, 4,354,002, 4,362,644, 4,370,255 and 4,534,880 which are hereby incorporated by reference to illustrate various of the anionic functional siliconates and to show methods for their preparation. The general form of an anionic siliconate can be represented by the formula:

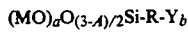

$$(MO)_a O_{(3-A)/2} Si-R-Y_b$$

wherein R is an organic linking group; Y represents anionic functional groups and the anionic functionality Y is positioned at least 2 and preferably at least 3 carbon atoms removed from the silicon atom; and b represents the number of anionic functional groups on the linking group and can vary from 1 to 3. In the formula M represents the cation of a strong base such as alkali metal cations or organoquaternary ammonium cations or M represents a hydrogen such that the siliconate may also contain silanol functionality. Generally a can vary from about 1 to 3.

It is preferred that a has the value of 3 to about 2 such that the anionic siliconate is predominately a monomeric species in aqueous solutions. Monomers are preferred. It should be understood however that oligomeric anionic siliconates where a is 1 to about 2 are also useful in the invention. Under alkaline conditions the oligomers are in equilibrium with the monomers. It should also be apparent that the equilibrium can be shifted toward monomeric species by the addition of alkali metal hydroxide to the aqueous solution of the siliconate.

The organic linking group R may contain other atoms in addition to carbon and hydrogen such as oxygen, sulfur and nitrogen. These atoms may be present as other functional groups such as ether, sulfide, hydroxy, amide or amine. Other functionality as represented by these atoms should be positioned at least 2 and preferably 3 or more carbon atoms removed from the site of silicon atom attachment in the linking group. Such positioning of functionality within the linking group provides substituents on silicon that are more stable and less readily cleaved. Generally it is preferred that the linking group contain from 2 to a maximum of about 16 carbon atoms. While linking groups with greater than 16 carbon atoms may be used in the invention, it is believed that the hydrophobic character produced by such linking groups reduce the effectiveness of the siliconates so that the linking groups with greater than 16 carbon atoms are less preferred.

Linking groups represented by R include polyvalent hydrocarbon radicals such as dimethylene, trimethylene, hexadecamethylene, phenylene, tolylene, xenylene, naphthylene and substituted polyvalent hydrocarbon radicals such as

—(CH$_2$)$_3$SCH—.

—(CH$_2$)$_3$OCH$_2$CH(OH)CH$_2$—, —(CH$_2$)$_3$SCH$_2$—,

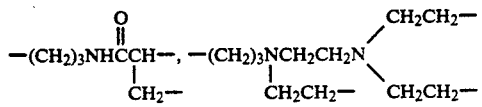

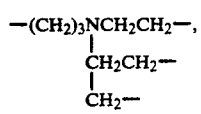

—CH$_2$CH(CH$_3$)CH$_2$NHCH$_2$CH$_2$N—CH$_2$— and
                                            |
                                           CH$_2$—

Generally when M is an alkali metal cation it is preferred that it be sodium because of its ready availability and low cost. Similarly the sodium salts of the oxyacids are preferred anionic functional groups in the siliconates.

Among the numerous anionic siliconates suitable include compositions conforming generally to the following formulas:

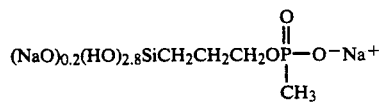

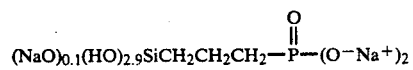

(NaO)$_{0.2}$(HO)$_{2.8}$Si(CH$_2$)$_6$SO$_3^-$Na$^+$

(HO)$_3$SiCH$_2$CH$_2$—C$_6$H$_5$—SO$_3^-$K$^+$ (KO)$_{0.2}$(HO)$_{2.8}$SiCH$_2$CH$_2$SCH$_2$COO$^-$K$^+$

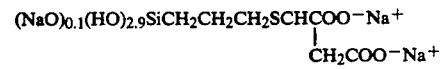

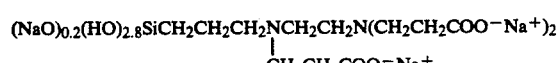

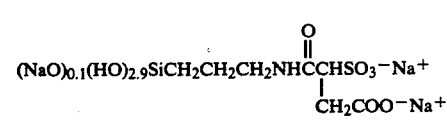

-continued (NaO)$_{0.2}$(HO)$_{2.8}$SiCH$_2$CH$_2$NCH$_2$CH$_2$N(CH$_2$SO$_3^-$Na$^+$)$_2$
                                    |
                                   CH$_2$SO$_3^-$Na$^+$ and (NaO)$_{0.2}$(HO)$_{2.8}$SiCH$_2$CH$_2$COO$^-$Na$^+$.

The following examples are set forth in order to further illustrate the concept of the present invention.

EXAMPLE I

A method was developed to measure the humectant/hygroscopic properties of materials as a function of relative humidities. The method was used to generate a screen of materials and correlate humectant ranking to glycerine a well known humectant.

Five constant humidity chambers were constructed as follows:

1. 0% R.H. using CaSO$_4$ (Drierite)
2. 35% R.H. using CaCl$_2$ saturated in H$_2$O
3. 52% R.H. using Na$_2$Cr$_2$O$_7$ saturated in H$_2$O
4. 66% R.H. using NaNO$_2$ saturated in H$_2$O
5. 86% R.H. using KHSO$_4$ saturated in H$_2$O The actual humidities of the chambers were not measured and a constant temperature was not maintained. A glycerine sample was included as a control with each new set of unknowns to account for any variation in temperature or humidity. The number of samples tested varied between four and eight. Weighed aliquots of each sample were added to weighed glass dishes with a filter paper in the bottom of each dish. The samples employed were water or methanol solutions. The quantity of solution was adjusted to provide about four grams of nonvolatile component following evaporation of the solvent. Each sample was heated in an oven at seventy-five degrees Centigrade for 3.5-5.5 hours in order to remove the majority of the solvent. The samples were placed in the 0% R.H. chamber and allowed to equilibrate to constant weight. The time to reach constant weight was 18-20 days. After equilibration at 0% R.H., the dry weight of the samples was recorded and the samples were placed in the 35% R.H. chamber. This procedure was repeated until the samples had been equilibrated in all of the chambers.

Two calculation modes were used for the data.

Weight % Increase at $X$ % R.H. =

$$\frac{(\text{Gm at }X\text{ \% R.H.})(\text{Gm at 0\% R.H.})}{(\text{Gm at 0\% R.H.})} \times 100 \text{ (Mode I)}$$

Mole H$_2$O/Mole $R$ at $X$% R.H. =

$$\frac{\frac{(\text{Gm at 0\% R.H.})(\text{wt \% inc. at }X\text{\% R.H.})}{(100 \times 18)}}{\frac{(\text{Gm at 0\% R.H.})(\text{Mole }R/\text{Mole Sample})}{\text{M. Wt. of Sample}}} \text{ (Mode II)}$$

where $X$ % R.H.=35%, 52%, 66%, 86% R.H. and R is an active group such as OH for glycerine or Na for the siliconate.

The composition of the siliconates tested are set forth in Table I.

TABLE I

| Material | Structure |
|---|---|
| 1 | (MeO)$_3$Si(CH$_2$)$_3$NR$_1$(CH$_2$)$_2$N(R$_1$)$_2$ |
| 2 | (NaO)$_3$Si(CH$_2$)$_3$NR$_2$(CH$_2$)$_2$N(R$_2$)$_2$ |

TABLE I-continued

| Material | Structure |
|---|---|
| 3 | Bu N $R_2$ $(CH_2)_2$ N $(R_2)_2$ |
| 4 | $(NaO)_3Si(CH_2)_3N(CH_3)R_2$ |
| 5 | $(KO)_3Si(CH_2)_3N(CH_3)R_3$ | where $R_1=CH_2CH_2COOMe$, $R_2=CH_2CH_2COONa$, $R_3=CH_2CH_2COOK$

Weight % Increase data was determined as a function of % R.H. and is set forth in the following table. Glycerine was included as a comparison.

TABLE I

| | | WEIGHT % INCREASE | | | |
|---|---|---|---|---|---|
| Material | Active Group | 35% R.H. | 52% R.H. | 66% R.H. | 86% R.H. |
| Glycerine | OH | 11.7 | 29.1 | 43.2 | 91.1 |
| 1 | OMe | — | — | 0 | 0.2 |
| 2 | ONa | 0 | 21.3 | 37.0 | 73.4 |
| 3 | ONa | 0 | 29.0 | 49.6 | 99.8 |
| 4 | ONa | 0 | 19.7 | 32.0 | 67.2 |
| 5 | OK | 15.2 | 32.2 | 41.0 | 65.3 |

The nonmetal salt 1 exhibited minimal humectancy properties. Conversion of the methylester to a metal salt dramatically increased the hygroscopicity of these materials. At about 52% RH these materials provide an alternative to glycerine. A comparison to glycerine was conducted based upon the level of active sites in the molecule. This data for mole ratio of $H_2O$/R-Group is set forth in Table II.

TABLE II

| | | | MOLE $H_2O$/MOLE R GROUP | | | |
|---|---|---|---|---|---|---|
| Material | R Group | M % R | 35% R.H. | 52% R.H. | 66% R.H. | 86% R.H. |
| Glycerine | OH | 3 | 0.2 | 0.5 | 0.7 | 1.6 |
| 2 | ONa | 6 | 0 | 1.0 | 1.8 | 3.6 |
| 3 | ONa | 3 | 0 | 2.1 | 3.6 | 7.4 |
| 4 | ONa | 4 | 0 | 0.8 | 1.4 | 2.9 |
| 5 | OK | 4 | 0.8 | 1.7 | 2.1 | 3.4 |

Based upon the number of active sites in the molecule, the siliconate materials demonstrated more efficient humectant properties than glycerine especially at 52% R.H. One disadvantage of glycerine as a humectant in skin care applications is its limited effectiveness at low relative humidities. These siliconates overcome this limitation and provide the inherent aesthetic benefits of organosilicon compounds.

EXAMPLE II

Example I was repeated except that a sixth constant humidity chamber was added which was 76% RH using $NaC_2H_3O_2$ saturated with water. In this example, two differing procedures were followed. One method involved adding weighed aliquots of each sample to weighed plastic petri dishes. The quantity of sample mixture was adjusted to 4.5-5.0 gm of non-volatile material after solvent evaporation. These samples were placed in an 80° C. oven for 16 hours to drive off the solvent. The samples were placed in a 0% R.H. chamber and allowed to equilibrate to constant weight. The time to reach constant weight was 18-20 days. After equilibration at 0% R.H., the dry weight of the samples was recorded and the samples placed in the 35% R.H. chamber. This procedure was repeated until the samples had been equilibrated in all chambers. The second method differed in that weighed aliquots of each sample were added to weighed glass dishes with a filter paper in the bottom of each dish. The filter paper acted as a membrane to maintain a thin film across the dish rather than allowing the sample to aggregate into a concentrated mass. These samples were heated in a 75° C. oven for 3.5-5.5 hours to remove the solvent. The samples were placed in the 0% R.H. chamber and the above procedure followed. The measured humectant properties are dependent upon the procedure and glycerine was included as a control with each set.

The composition of the siliconates tested is set forth below in Table III.

TABLE III

| Material | Structure |
|---|---|
| 1 | $(MeO)_3Si(CH_2)_3OPO(CH_3)OMe$ |
| 2 | $(NaO)_3Si(CH_2)_3OPO(CH_3)ONa$ |
| 3 | $(NH_4O)_3Si(CH_2)_3OPO(CH_3)ONH_4$ |
| 4 | $(NaO)_3Si(CH_2)_3OPO(CH_3)ONa$ |
| 5 | $(KO)_3Si(CH_2)_3OPO(CH_3)OK$ |

Weight % increase data was collected as a function of % R.H. for the thin film procedure using filter paper in the dishes and is shown in the following table. Glycerine is included for comparison.

TABLE IV

| | | Weight % Increase | | | |
|---|---|---|---|---|---|
| Material | Active Group | 35% R.H. | 52% R.H. | 66% R.H. | 86% R.H. |
| Glycerine | OH | 11.7 | 29.1 | 43.2 | 91.1 |
| 1 | OMe | 3.2 | 6.9 | 9.2 | 15.0 |
| 2 | ONa | 10.1 | 30.6 | 38.9 | 73.0 |

The sodium phosphonate salt exhibited a humectancy profile comparable to glycerine except at 86% R.H. The humectant behavior at 86% R.H. is however of minimal concern in dry skin applications. The phosphonate ester is hygroscopic to a lesser extent.

The weight % increase date collected as a function of % R.H. for the first sample procedure with no filter paper is shown in the following table.

TABLE V

| | | Weight % Increase | | |
|---|---|---|---|---|
| Material | Active Group | 35% R.H. | 52% R.H. | 76% R.H. |
| Glycerin | OH | 16.1 | 35.9 | 65.9 |
| 3 | $ONH_4$ | 7.5 | 15.9 | 25.4 |
| 4 | ONa | 15.4 | 48.1 | 79.9 |
| 5 | OK | 37.0 | 71.3 | 104.7 |

A general increase in humectancy was observed from $NH_4$ to Na to the K phosphonate salt. The potassium salt exhibited a two-fold increase in hygroscopicity over glycerine.

A comparison of the activity of the phosphonate salts with glycerine on a mole ratio basis is shown in the following table.

TABLE VI

| | | | Mole $H_2O$/Mole R Group | | |
|---|---|---|---|---|---|
| Material | R Group | M % R | 35% R.H. | 52% R.H. | 76% R.H. |
| Glycerine | OH | 3 | 0.3 | 0.6 | 1.1 |
| 3 | $ONH_4$ | 4 | 0.3 | 0.6 | 1.0 |
| 4 | ONa | 4 | 0.6 | 2.0 | 3.4 |
| 5 | OK | 4 | 1.9 | 3.6 | 5.4 |

Based upon the number of active sites/molecule the phosphonate salts demonstrate hygroscopicity equal to or greater than glycerine. The sodium and potassium salts are more active at lower relative humidities than glycerine which is beneficial for dry skin applications.

No standard method has been accepted in the skin care industry to define the moisturization properties of a particular ingredient. Different properties of moisturizers can be measured such as humectancy and occlusivity. A reduction in the loss of water from the skin surface or occlusivity contributes to increased softness and flexibility of skin. The occlusive properties of an ingredient can be measured using a Servo-Med Evaporimeter to determine the reduction in transepidermal water loss (% TWL) caused by the ingredient relative to untreated skin. Data was collected for siliconates applied as formulated products, from a solution, and "neat", and the results were compared to a well known occlusive agent petrolatum.

EXAMPLE III

An in vitro sample chamber was constructed from a one pint wide-mouthed glass bottle filled with $K_2SO_4$ saturated water. The bottle was covered with a sandwich arrangement of a wire mesh screen which supported sample substrates overlaid with an aluminum foil liner with holes cut for the sample substrates, and an open-topped screw lid to fix the arrangement to the bottle. The sample substrates were one-inch circles cut from about 1.25 mm thick filter paper. The holes cut in the aluminum foil liner were of the same diameter as the probe on the Evaporimeter. Sample chambers with either two or four holes were used. The experiments were conducted in a controlled humidity room. The range of relative humidities was between 15% and 30%. The $K_2SO_4$ saturated water inside the chamber provided a 97% R.H. to simulate the interior water reservoir of skin. The sample substrate weights were recorded and the sample chamber was assembled. Background date $(WE)_0$ for each sample site was collected by placing the Evaporimeter probe over the site and recording the readings for two minutes at each site. An average of the readings for each site defined the baseline for each site. The sample substrates were removed from the chamber. A weighed quantity of material was applied as a uniform film across each substrate. The material was applied either as a "neat" film or from a solution. With solutions, the substrates were placed in a 90° C. over for 45 minutes after application to remove the solvent. The substrates were reassembled in the sample chamber and allowed to equilibrate for about 30 minutes. Treated site data $(WE)_1$ was collected at intervals until constant readings were achieved. % TWL reduction data was calculated for each site using the equation:

$$\% \ TWL \ Reduction = \frac{(WE)_1 - (WE)_0}{(WE)_0} \times 100$$

The measured % TWL reduction was dependent upon the application form which was neat or in solution. Application of small quantities of petrolatum neat to the sample substrates produced a substantial reduction in % TWL. However if petrolatum was applied from solution, the efficiency of % TWL reduction was decreased. The phosphonate materials were water or methanol solutions. The petrolatum solution occlusivity data was used for comparative purposes.

The % TWL reduction data for the phosphonate structures of Table III exhibited an increase in % TWL Reduction with increasing quantities of material. A direct comparison to petrolatum is shown in the following table for a constant loading of 80 mg applied from solution.

TABLE VII

| Material | Active Group | % TWL Reduction (80 mg) |
|---|---|---|
| Petrolatum | $CH_2$ | 18 |
| 1 | OMe | 26 |
| 3 | $ONH_4$ | 34 |
| 4 | ONa | 70 |
| 5 | OK | 92 |

The siliconates of Table VII exhibited occlusivity to a greater extent than petrolatum.

It will be apparent from the foregoing that many other variations and modifications may be made in the compounds, compositions and methods described herein without departing substantially from the essential features and concepts of the present invention. Accordingly, it should be clearly understood that the forms of the invention described herein are exemplary only and are not intended as limitations on the scope of the present invention as defined in the appended claims.

That which is claimed is:

1. A method of treating dry human skin comprising applying to skin an organosilicon compound exhibiting humectant-like characteristics, the organosilicon compound being an anionic functional siliconate having the formula $$(MO)_aO_{(3-a)/2}Si-R-Y_b$$

in which M is an alkali metal cation; R is an organic linking group; Y is an alkali metal salt of an oxyacid and Y is positioned at least two carbon atoms removed from the silicon atom; a and b are integers each having a value of from one to three.

2. The method of claim 1 in which the organosilicon compound is applied to the skin in the presence of a solvent.

3. The method of claim 1 in which the organosilicon compound is applied to the skin in the absence of a solvent.

4. The method of claim 1 in which the organosilicon compound is applied to the skin as a formulated product.

5. The method of claim 1 in which the organosilicon compound is selected from the group consisting of $(NaO)_3Si(CH_2)_3NR''(CH_2)_2N(R'')_2$; $(NaO)_3Si(CH_2)_3N(CH_3)R''$; $(KO)_3Si(CH_2)_3N(CH_3)R'''$; $(NaO)_3Si(CH_2)_3OPO(CH_3)ONa$; and $(KO)_3Si(CH_2)_3OPO(CH_3)OK$; R'' is $-CH_2CH_2COONa$, and R''' is $-CH_2CH_2COOK$.

6. A method of treating dry human skin comprising applying to skin an occlusive film forming organosilicon compound, the organosilicon compound being an anionic functional siliconate having the formula $$(MO)_aO_{(3-a)/2}Si-R-Y_b$$

in which M is an alkali metal cation; R is an organic linking group; Y is an alkali metal salt of an oxyacid and Y is positioned at least two carbon atoms removed from the silicon atom; a and b are integers each having a value of from one to three.

7. The method of claim 6 in which the organosilicon compound is applied to the skin in the presence of a solvent.

8. The method of claim 6 in which the organosilicon compound is applied to the skin in the absence of a solvent.

9. The method of claim 6 in which the organosilicon compound is applied to the skin as a formulated product.

10. The method of claim 6 in which the organosilicon compound is selected from the group consisting of $(NaO)_3Si(CH_2)_3OPO(CH_3)ONa$; $(KO)_3Si(CH_2)_3OPO(CH_3)OK$.

* * * * *